United States Patent [19]

Olander

[11] 4,205,007

[45] May 27, 1980

[54] MANGANESE COMPLEXES OF SALICYL-ALDEHYDE-ALKANOLIMINES AS CATALYSTS FOR THE POLYMERIZATION OF 2,6-DI-SUBSTITUTED PHENOLS

[75] Inventor: Walter K. Olander, Clifton Park, N.Y.

[73] Assignee: General Electric Company, Pittsfield, Mass.

[21] Appl. No.: 880,135

[22] Filed: Feb. 22, 1978

Related U.S. Application Data

[62] Division of Ser. No. 753,506, Dec. 21, 1976, Pat. No. 4,093,597.

[51] Int. Cl.$^2$ ............................................. C07F 00/00
[52] U.S. Cl. ............................... 260/429 C; 260/429 J
[58] Field of Search .......................... 260/429 J, 429 C

[56] References Cited

U.S. PATENT DOCUMENTS

| | | | |
|---|---|---|---|
| 2,116,913 | 5/1938 | Schmidt et al. | 260/429 J |
| 3,248,410 | 4/1966 | Berenbaum | 260/429 J |

*Primary Examiner*—Lester L. Lee
*Attorney, Agent, or Firm*—Morgan, Finnegan, Pine, Foley & Lee

[57] ABSTRACT

A novel catalyst is disclosed that is useful in the oxidative coupling of phenolic monomers. The catalyst is a manganese chelate that is derived from a salicylaldehyde-alkanolimine.

4 Claims, No Drawings

MANGANESE COMPLEXES OF SALICYL-ALDEHYDE-ALKANOLIMINES AS CATALYSTS FOR THE POLYMERIZATION OF 2,6-DI-SUBSTITUTED PHENOLS

This is a division of application Ser. No. 753,506, filed Dec. 21, 1976, and now U.S. Pat. No. 4,093,597 issued June 6, 1978.

This invention provides a new and novel catalyst that is useful for catalyzing the oxidative coupling of a phenolic monomer. The catalyst is a manganese chelate that is derived from a silicylaldehyde-alkanolimine.

BACKGROUND OF THE INVENTION

The polyphenylene oxides and methods for their preparation are known in the art and are described in numerous publications, including Hay U.S. Pat. No. 3,306,874 and U.S. Pat. No. 3,306,875. The Hay processes are based on the use of copper-amine complex catalysts. Manganese based catalysts for the oxidative coupling of phenolic monomers in the formation of polyphenylene oxides are disclosed in McNelis, U.S. Pat. No. 3,220,979; Nakashio, U.S. Pat. No. 3,573,257; Nakashio, U.S. Pat. No. 3,787,361 and Olander, U.S. Pat. No. 3,956,242. In the applicant's copending applications Ser. No. 491,475 filed July 24, 1974 and Ser. No. 534,903 filed Dec. 20, 1974, there are disclosed novel procedures for polymerizing polyphenylene oxides with complex manganese based catalysts. All of these patents and applications are hereby incorporated by reference.

In U.S. Pat. No. 3,444,133 and U.S. Pat. No. 3,455,880, there are disclosed manganese chelates of bis-salicylaldehyde ethylene diimine which are reported to be useful in the preparation of polyphenylene oxides. Japanese printed patent application Nos. 26396/73 and 26398/73 also disclose catalysts which may be manganese or cobalt complexes of one or more compounds selected from the group consisting of primary amines and aliphatic, alicyclic and aromatic aldehydes. None of these citations disclose a manganese chelate having a salicylaldehyde-alkanolimine component or suggest its use in the oxidative coupling of phenolic moners under basic conditions.

Accordingly, it is a primary object of this invention to provide a novel manganese catalyst for the oxidative coupling of phenolic monomers.

DETAILED DESCRIPTION OF THE INVENTION

The present invention provides a novel catalyst for the oxidative coupling of phenolic monomers. The novel catalyst is a compound of the formula:

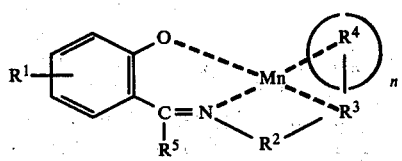

wherein $R^1$ is selected from hydrogen, lower alkyl of from 1 to 8 carbon atoms and phenyl; halogen, lower alkoxy of from 1 to 8 carbon atoms; $R^2$ is o-phenylene; lower alkoxy o-phenylene wherein the lower alkoxy group has from 1 to 8 carbon atoms; halo-o-phenylene; lower alkyl o-phenylene wherein the lower alkyl group has from 1 to 8 carbon atoms; lower alkylene of from 2 to 3 carbon atoms; phenyl lower alkylene wherein the alkylene portion has from 2 to 3 carbon atoms and lower alkyl substituted lower alkylene wherein the lower alkyl group has from 1 to 8 carbon atoms and the alkylene portion has from 2 to 3 carbon atoms; $R^3$ is oxygen or nitrogen; $R^4$ is lower alkyleneoxy having from 2 to 3 carbon atoms, lower alkyl substituted alkyleneoxy wherein the lower alkyl group has from 1 to 8 carbon atoms and the alkylene portion has from 2 to 3 carbon atoms, o-phenyleneoxy, phenyl lower alkyleneoxy wherein the alkylene group has from 2 to 3 carbon atoms lower-alkyl-o-phenylene wherein the lower alkyl group has from 1 to 8 carbon atoms or phenyl-o-phenyleneoxy; $R^5$ is selected from hydrogen, lower alkyl of 1 to 8 carbon atoms or phenyl; and n is 0 or 1.

Included within the scope of Formula I compounds of the formula:

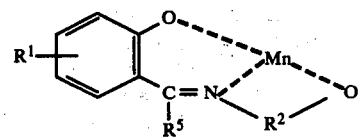

wherein $R^1$ is selected from hydrogen, lower alkyl of from 1 to 8 carbon atoms and phenyl; and $R^2$ is lower alkylene of from 2 to 3 carbon atoms or o-phenylene. The preferred species of this formula are those componds wherein $R^1$ is hydrogen and $R^2$ is ethylene or o-phenylene and $R^5$ is hydrogen or methyl.

Also included within the scope of Formula I are compounds of the formula:

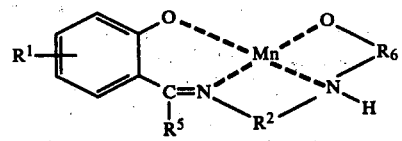

wherein $R^1$, $R^2$ and $R^5$ are as hereinabove defined; and $R^6$ is lower alkylene of 2 or 3 carbon atoms or o-phenylene.

As used herein and in the appended claims the term lower alkyl of from 1 to 8 carbon atoms includes both straight and branched chain hydrocarbon groups such as methyl, ethyl, propyl, hexyl, iso-propyl and the like. The term halogen includes chlorine, bromine, fluorine and iodine. The term lower alkoxy includes methoxy, ethoxy, i-propxy, butoxy, hexoxy and the like. The term lower alkylene of from 2 to 3 carbon atoms includes groups such as -CH$_2$-CH$_2$-; -CH$_2$-CH$_2$-CH$_2$;

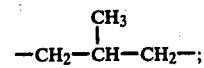

and the like. The term phenyl lower alkylene wherein the alkylene portion has from 2 to 3 carbon atoms includes groups such as

and the like.

The imine component of the novel catalysts of the invention may be prepared by reacting a salicylaldehyde or an appropriate o-hydroxy ketone with an alkanolamine according to the following reaction scheme;

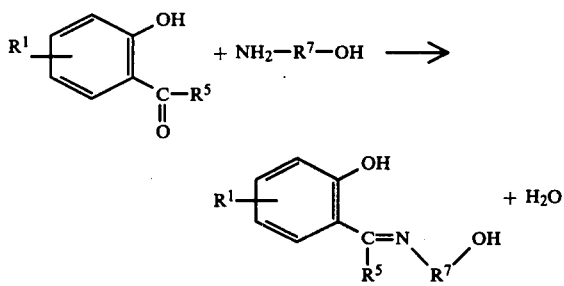

wherein R[1] and R[5] are the same as hereinabove defined; R[7] is o-phenylene; lower alkoxy o-phenylene wherein the lower alkoxy group has from 1 to 8 carbon atoms; halo-o-phenylene; lower alkyl o-phenylene wherein the lower alkyl group has from 1 to 8 carbon atoms; lower alkylene of from 2 to 3 carbon atoms; phenyl lower alkylene wherein the alkylene portion has from 2 to 3 carbon atoms; lower alkylene amine lower alkylene wherein the lower alkylene portions have from 2 to 3 carbon atoms; o-phenylene amine lower alkylene wherein the lower alkylene portion has from 2 to 3 carbon atoms; and o-phenylene amino-o-phenylene or substituted derivatives thereof.

Generally the imine may be prepared by heating the salicylaldehyde component with the primary alkanolamine in an appropriate solvent such as benzene or a lower alkanol of 1-6 carbon atoms, i.e. methanol. If desired the manganese salt may be added after the imine is prepared or the manganese salt, the salicylaldehyde and the primary alkanolamine may all be combined to form the manganese imine chelate in a single step.

Generally, it is preferred to employ substantially stoichiometric amounts of the chelate forming materials although it may be desirable to utilize an excess of the imine forming components to insure substantially complete chelation of the manganese salt.

The suitable manganese salts include the manganese (II) halides such as manganese (II) chloride (also known as manganous chloride) manganese (II) bromide, manganese (II) iodide, etc., as well as other manganese (II) compounds, such as manganese carbonate, manganese (II) oxalate, manganese (II) sulfate, manganese (II) nitrate, manganese (II) phosphates, etc., including hydrated forms thereof.

The chelate compounds may be formed by reacting substantially equal amounts of the manganese (II) salt and the imine in the presence of a suitable solvent such as a lower alkanol of 1 to 6 carbon atoms such as methanol. Higher stoichiometries may be employed such as 2 moles of alkanolamine per mole of manganese.

The imine may be formed from primary aminoalkanols such as ethanolamine; o-aminophenol; 2-(2-aminoethylamine) ethanol; 1-phenyl-2-aminoethanol; 1-methyl-2-aminoethanol. Salicylaldehyde per se or its substituted derivatives may be employed in the formation of the imine.

The process in which the novel manganese based catalyst may be employed to catalyze the oxidative coupling of phenolic monomers may be carried out by combining the catalyst and monomer in an appropriate organic solvent in the presence of an oxygen containing gas and alkali. Generally, polymerizations may be carried out by combining the catalyst and monomer in an appropriate organic solvent in the presence of an oxygen containing gas. Generally, polymerizations may be carried out using a mole ratio of phenolic monomer to complexed manganese of from 100:1 to 300:1.

The preferred polymerization solvent is a mixture of a lower alkanol of 1 to 6 carbon atoms, i.e. methanol and an aromatic organic solvent such as toluene, benzene, chlorobenzene, xylene or styrene. The preferred reaction composition of a phenolic monomer, i.e., 2, 6-xylenol, a lower alkanol, i.e. methanol, and an aromatic organic solvent is from 20:20:60 to 16:10:74 weight percent respectively. The exact ratios are not critical and may be varied depending on the particular catalyst employed.

The catalyst is dissolved in a lower alkanol such as methanol and is added to the phenolic monomerorganic solvent solution in a reactor that is equipped with an oxygen inlet tube and an appropriate stirring device. In order to increase the stability and reactivity of the catalyst, primary, secondary or tertiary amines such as n-hexylamine may be added to the reaction mixture according to the procedure described in U.S. Pat. No. 3,956,242, which is hereby incorporated by reference. Various amines are mentioned in U.S. Pat. No. 3,306,874 and mole ratio within the range of from about 100:0.05 to about 100:15.

The polymerization is initiated by introducing a stream of oxygen at a rate that is sufficient to be in excess over that which is absorbed. Alkali is essential and is preferably added as a 50% aqueous solution of sodium hydroxide sufficient to maintain a mole ratio of 14:1 to 18:1 and more preferably about 16:1 of phenolic compound to hydroxyl ion during the polymerization. Other basic materials are described in U.S. Pat. No. 3,956,242. After initiation of the reaction, the temperature does not exceed substantially 45° C., preferably 35° C. When a polyphenylene oxide having an intrinsic viscosity of about 0.45 dl/g as measured in chloroform at 30° C. is obtained, the reaction may be terminated by adding the reactor, sufficient aqueous acetic acid or aqueous sulfuric acid to neutralize the reaction media. After neutralization, the entire reaction mixture may be precipitated with a suitable solvent, e.g. methanol, and isolated according to standard techniques.

DESCRIPTION OF THE PREFERRED EMBODIMENTS

The following examples illustrate the process of the invention. They are merely illustrative, and are not to be construed to limit the invention in any manner whatsoever.

EXAMPLE 1

An imine was formed by condensation of equimolar (0.8196 moles) amount of salicylaldehyde and ethanolamine in about 300 ml of toluene under nitrogen. The mixture was refluxed to remove the theoretical water of reaction in an apparatus equipped with a Dean-Stark trap. The catalyst was prepared using 41.7 g of this solution containing 3.03 g (0.0184 moles) of the imine.

A polymerization reaction was carried out with the following materials:
toluene: 578 ml
methanol: 105 ml
2,6-xylenol: 112 g (16% solids) (0.918 moles)

sodium hydroxide: 4.5 g (50% aq.)
MnCl$_2$: 2.31 g (0.0184 moles)
imine: (41.7 g of toluene solution containing 3.03 g of the imine prepared hereinabove to give a 1:1 complex with manganese)

The 2,6-xylenol, 534 ml of toluene and most of the methanol and all of the sodium hydroxide solution were charged into a 1 liter reactor equipped with an oxygen delivery tube and an overhead stirring motor. The catalyst solution comprised of manganese (II) chloride dissolved in methanol and the toluene solution of the imine formed from salicylaldehyde and ethanolamine were charged into the reactor and the polymerization run as a bulk reaction. After 4 hours the reaction is terminated by the addition of aqueous acetic acid. The intrinsic viscosity of the poly (2,6-dimethyl-1,4-phenylene oxide) is 0.21 dl/g as measured in chloroform at 30° C.

EXAMPLE 2

The procedure of Example 1 was repeated with the exception that 2.0 g of n-hexylamine (0.02 mole) is added to the polymerization mixture and the polymerization was terminated after 4 hours. The intrinsic viscosity of the poly (2,6-dimethyl-1,4-phenylene oxide) is 0.50 dl/g as measured in chloroform at 30° C. This clearly demonstrates the rate enhancing effect of ancillary amines.

EXAMPLE 3

A catalyst is prepared in situ by the condensation of 0.799 g of salicylaldehyde (0.00656) mole and 0.898 g of 1-phenyl-2-aminoethanol (0.00656 mole) in methanol in the presence of 0.825 g of manganese (II) chloride (0.00656 mole). The catalyst was used directly in the polymerization described below. The following materials were employed:
toluene: 390 ml
methanol: 100 ml
2,6-xylenol: 80 g (0.6557 moles)
sodium hydroxide: 3.2 g (50% aq.)
n-hexylamine: 1.0 g The ratio of 2,6-xylenol to manganese was 100:1. A bulk polymerization was carried out at 30° C. for 170 minutes at which time the polymer had an intrinsic viscosity of 0.34 dl/g as measured in chloroform at 30° C.

EXAMPLE 4

An imine was formed by the condensation of 22.35 g of salicylaldehyde and 20 g of o-aminophenol in toluene. The mixture was refluxed and the water of reaction was collected in a Dean-Stark trap. The imine precipitated upon cooling. The imine was employed in a 2,6-xylenol polymerization using the following materials:
methanol: 87.5 ml
chlorobenzene: 320 ml
2,6-xylenol: 80.0 g (0.6557 moles)
sodium hydroxide: 2.4 g (50% aq.)
n-hexylamine: 0.8 g (0.0079 moles)
MnCl$_2$: 0.825 g (0.0065 moles)
imine (MW 223): 1.46 g (0.0065 moles)

A bulk polymerization is carried out for 41 minutes which results in a poly (2,6-dimethyl-1,4-phenylene oxide) having an intrinsic viscosity of 0.35 dl/g as measured in chloroform at 30° C.

EXAMPLE 5

An imine was prepared by refluxing 10.0 g of salicylaldehyde and 8.85 g of o-(2-aminoethylamino) ethanolamine in toluene for minutes. Thereafter the solvent is stripped off and the yellow product is washed with ether. This imine was employed to prepare poly (2,6-dimethyl-1,4-phenylene oxide) using the following materials:
chlorobenzene: 393 ml
methanol: 90 ml
2,6-xylenol: 96 g (0.786 moles)
sodium hydroxide: 3.84 g (50% aq.)
n-hexylamine: 1.0 g (0.010 moles)
MnCl$_2$: 0.99 g (0.0078 moles)
imine: 1.58 g (0.0078 moles)

A bulk polymerization was carried out for 97 minutes which resulted in a poly (2,6-dimethyl-1,4-phenylene oxide) having an intrinsic viscosity of 0.24 dl/g as measured in chloroform at 30° C.

EXAMPLE 6

An imine is prepared by refluxing 2.0 g of 1-phenyl-2-aminoethanol and 1.82 g of salicylaldehyde in 100 ml of toluene for several hours. The reaction solution is diluted to a final volume of 100 ml and used directly in a polymerization using the following materials:
2,6-xylenol: 160 g (1.31 moles)
methanol: 120 ml
toluene: 534 ml
MnCl$_2$: 1.64 g (0.0131 moles)
NaOH: 8.5 g (50% aq.)
Gi-methyl-n-butyl amine: 1.32 g (0.0131 moles)
imine solution: 89 ml A polymerization is carried out in a one liter reactor according to the general procedure of Example 5. The manganese chloride in 50 ml of methanol is combined with the toluene solution of the imine for 10 minutes. The di-methyl-n-butyl amine is added and the mixture is stirred for 30 minutes. The catalyst solution is added to the polymerization reactor containing the remaining solvent, base and 2,6-xylenol. The polymerization reaction is maintained at 25°-33° C. for 93 minutes, and is quenched with 20 ml of 50% aqueous acetic acid. The isolated poly (2,6-di-methyl-1,4-phenylene oxide) has an intrinsic viscosity of 0.39 dl/g as measured in chloroform at 30° C.

Although the above examples have shown various modifications of the present invention, other variations are possible in light of the above teachings. It is, therefore, to be understood that changes may be made in the particular embodiments of the invention described which are within the full intended scope of the invention as defined by the appended claims.

I claim:
1. A catalyst for the oxidative coupling of a phenolic monomer which comprises a compound of the formula:

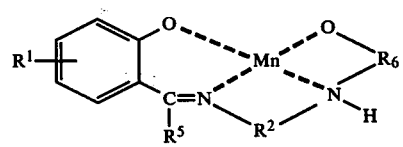

wherein R$^1$ and R$^5$ are selected from the group consisting of hydrogen, lower alkyl of from 1 to 8 carbon atoms and phenyl; and $R^2$ and $R^6$ are independently lower alkylene of from 2 to 3 carbon atoms or o-phenylene.

2. A catalyst as defined in claim 1 wherein $R^1$ and $R^5$ are hydrogen and $R^2$ and $R^6$ are independent selected from the group consisting of lower alkylene of 2 or 3 carbon atoms alkyl substituted lower alkylene of 2 to 3 carbon atoms alkyl substituted lower alkylene of 2 to 3 carbon atoms or o-phenylene.

3. A catalyst for the oxidative coupling of a phenolic monomer which comprises a compound of the formula:

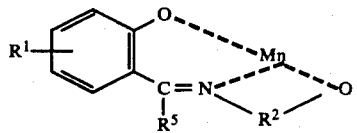

wherein $R^1$ and $R^5$ are hydrogen and $R^2$ is ethylene.

4. A catalyst as defined in claim 2 wherein $R^2$ and $R^6$ are ethylene.

* * * * *

UNITED STATES PATENT AND TRADEMARK OFFICE
CERTIFICATE OF CORRECTION

PATENT NO. : 4,205,007

DATED : May 27, 1980

INVENTOR(S) : Walter Karl Olander

It is certified that error appears in the above—identified patent and that said Letters Patent is hereby corrected as shown below:

In Column 1, line 12, "silicylaldehyde" should read --salicylaldehyde--;

In Column 3, line 33, "sclvent" should read --solvent--;

In Column 4, lines 27-28 should read: --3,306,874 and U.S. Patent No. 3,306,875. The amine may be added at a phenol to amine mole ratio within the range of from about 100:0.05 to about 100:15--;

UNITED STATES PATENT AND TRADEMARK OFFICE
CERTIFICATE OF CORRECTION

PATENT NO. : 4,205,007
DATED : May 27, 1980
INVENTOR(S) : Walter K. Olander

It is certified that error appears in the above—identified patent and that said Letters Patent is hereby corrected as shown below:

In Column 7, Claim 2, delete second occurrence of "carbon atoms alkyl substituted lower alkylene of 2 to 3".

Signed and Sealed this

Twenty-fifth Day of August 1981

[SEAL]

Attest:

GERALD J. MOSSINGHOFF

Attesting Officer

Commissioner of Patents and Trademarks